United States Patent [19]

Comparetto

[11] Patent Number: 5,035,698
[45] Date of Patent: Jul. 30, 1991

[54] ARCUATE OSTEOTOMY BLADE

[75] Inventor: John E. Comparetto, Cincinnati, Ohio

[73] Assignee: Ohio Medical Instrument Co., Inc., Cincinnati, Ohio

[21] Appl. No.: 514,735

[22] Filed: Apr. 26, 1990

Related U.S. Application Data

[60] Division of Ser. No. 308,257, Feb. 8, 1989, Pat. No. 4,952,214, which is a continuation-in-part of Ser. No. 841,948, Mar. 20, 1986, abandoned, which is a continuation-in-part of Ser. No. 749,475, Jun. 27, 1985, Pat. No. 4,664,102, and a continuation-in-part of Ser. No. 721,640, Apr. 10, 1985, Pat. No. 4,708,133.

[51] Int. Cl.$^5$ .................... A61B 17/14; A61B 17/56
[52] U.S. Cl. .................................. 606/82; 606/79
[58] Field of Search ............ 606/82, 79, 84, 176–179; 83/745, 835

[56] References Cited

U.S. PATENT DOCUMENTS

| | | | |
|---|---|---|---|
| 21,411 | 9/1858 | Forman | 33/26 |
| 2,823,709 | 2/1958 | Konieczka | 83/745 |
| 4,069,824 | 1/1978 | Weinstock | 128/317 |
| 4,150,675 | 4/1979 | Comparetto | 128/305 |
| 4,335,715 | 6/1982 | Kirkley | 128/92 VY |
| 4,409,973 | 10/1983 | Neufeld | 606/179 X |
| 4,433,681 | 2/1984 | Comparetto | 128/92 VY |
| 4,501,268 | 2/1985 | Comparetto | 128/92 VY |
| 4,502,474 | 3/1985 | Comparetto | 128/92 VY |
| 4,509,511 | 3/1985 | Neufeld | 128/92 VY |
| 4,608,898 | 9/1986 | Volk | 83/745 |
| 4,627,425 | 12/1986 | Reese | 128/92 VY |
| 4,632,102 | 12/1986 | Comparetto | 128/92 VY |
| 4,664,102 | 5/1987 | Comparetto | 128/92 VY |
| 4,708,133 | 11/1987 | Comparetto | 128/92 VY |

FOREIGN PATENT DOCUMENTS 568769  4/1945  United Kingdom ................. 33/565

OTHER PUBLICATIONS

The Osteoguide System, J. E. Comparetto, Comparetto Ideas, Inc.

Primary Examiner—Robert A. Hafer
Assistant Examiner—Kevin G. Rooney
Attorney, Agent, or Firm—Wood, Herron & Evans

[57] ABSTRACT

A bone saw guide apparatus and method for positioning sequential saw cuts facilitates the cutting of a wedge of bone, in the correction of an angular bone deformity. An arcuate saw blade having a shaft which is parallel to its cutting edge provides greater blade strength and better control of the cut.

7 Claims, 3 Drawing Sheets

ARCUATE OSTEOTOMY BLADE

This application is a division of my co-pending application Ser. No. 308,257, filed Feb. 8, 1989, titled "Arcuate Osteotomy Blade, Blade Guide, and Cutting Method," now U.S. Pat. No. 4,952,214, which was a continuation-in-part of application Ser. No. 841,948, titled "The X-Osteoguide, and Arcuate Bone Cutters," filed Mar. 20, 1986, now abandoned, which was in turn a continuation-in-part of application Ser. No. 721,640, titled "Arcuate Bone Cutter and Wedge Guide System," filed Apr. 10, 1985, now U.S. Pat. No. 4,708,133, issued Nov. 24, 1987 and also a continuation-in-part application of application Ser. No. 06/749,475, filed June 27, 1985, now U.S. Pat. No. 4,664,102.

FIELD OF THE INVENTION

This invention relates to the making of cuts in the bone of a patient for the purpose of correcting an angular bone deformity.

THE PRIOR ART

Curved osteotomy cuts have been made with great difficulty by the use of oscillating saws and various types of blades. One prior method was to use a template having a series of holes that described a desired arc. The template was used to position a series of drill holes in bone that were then connected by sawing in connect-the-dots fashion.

Reese U.S. Pat. No. 4,627,425 discloses an apparatus with two separate guides for removing a straight-sided wedge of bone, wherein a first cut is made with a first guide, the cut being through the full thickness (depth) of the bone, a follower is placed in the first cut and a second guide is positioned at a desired angle to the follower and a second cut is made to free a wedge shaped section. The bone is not cut across its complete width; and no arcuate osteotomy is performed.

OBJECTS OF THE INVENTION

Broadly, the objective of this invention has been to provide an improved cutting blade, a more precise and more easily used guide apparatus, and an improved method of performing an osteotomy.

More specifically, an object of the invention has been to provide a stronger, more controllable, and more accurate bone cutting blade for use with a reciprocating saw.

A further object of the invention has been to provide a blade cutting guide for making straight and/or arcuate cuts in performing an osteotomy, and which will enable such cuts to be made more precisely.

A still further object of this invention has been the provision of a better method for making cuts to remove a wedge-shaped piece of bone to correct an angular deformity.

BRIEF DESCRIPTION OF THE INVENTION

The osteotomy saw guide of this invention presents two intersecting slots. The main slot is arcuate and is used in making a curved cut in a bone; the other slot may be either straight or arcuate and is used in cutting out a wedge-shaped section from the bone. The two slots cross or intersect, like an "X". The slots guide a saw blade, which may be either straight or curved and which passes through one or both slots, to make arcuate and/or straight cuts in a bone.

In making an osteotomy in accordance with the method of this invention, an arcuate cut is first made which extends from one side of the bone across part of its width. A wedge-shaped section, extending from the arc to the side of the bone, is then cut out and removed. The two segments of the severed bone are articulated about the arc, to close the gap left by removal of the wedge. The abutting arcuate surfaces provide a larger load-bearing area and improve regrowth of the bone (further discussion of the arcuate osteotomy technique is set forth in my prior U.S. Pat. No. 4,501,268, issued Feb. 26, 1985).

To facilitate making such cuts, the guide of this invention is preferably positioned on the bone by a bone pin which passes through a pivot hole offset from the slots. With the guide secured to the bone, the arcuate cut is made by guiding a blade along the main slot; a first wedge-forming cut is made by moving a blade along the second slot, to intersect the arcuate cut. The first wedge-forming cut is made only partially through the thickness of the bone; it should not cut the entire thickness of the bone, which would completely sever the bone across its width and thereby make it much more difficult to precisely define the wedge angle and accurately position the second wedge-forming cut. A zero locator or marker is placed through the guide where the two slots intersect and into the bone at the intersection of the cuts. The guide is then rotated about its pivot point to reposition the second slot a desired angular distance from its initial position over the first wedge cut; this angle should be selected to correspond to the degree of crook or deformity to be removed from the bone. A second wedge-forming cut is then made by guiding the saw blade along the second slot in its thus shifted position. This second wedge cut is made through the thickness of the bone; the bone is thereby completely severed into two segments. The first wedge cut is then completed by sawing through it to sever the wedge. The bone segments are then articulated about the curved cut to "close" the wedge-shaped gap and thereby reposition the bone segments in a new, straightened position for regrowth.

An arcuate saw blade is also provided, for use with or without the guide and method of the invention. The blade has a body which is cylindrically curved (like a segment of the wall of a cylinder, on an arc having a specific radius of curvature) and which presents bone cutting teeth along an edge thereof which is transverse to the radius of curvature. A driving shank, narrower than the blade, is affixed to the blade parallel to and preferably directly in line with the cutting edge. This configuration provides improved resistance to twist and deflection of the blade in cutting. The body of the blade trails behind the cutting edge and tracks in the arcuate slot as it is being cut, to form a curved cut of radius corresponding to the curvature of the blade. The shank may have a non-circular geometrical cross-sectional shape, by which it can be confined in a given orientation in a swing arm, for cutting arcs of different radii and with surfaces which will tightly mate for regrowth.

DETAILED DESCRIPTION OF THE INVENTION

Figure 1:
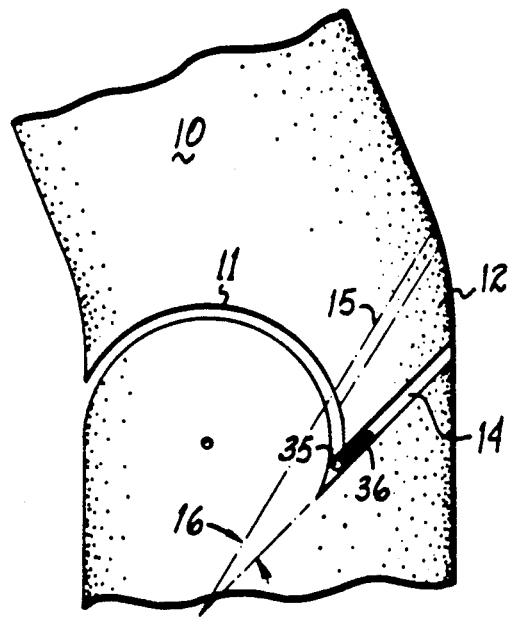
FIG. 1 is a diagrammatic fragmentary plan view of a portion of a bone in which an arcuate cut and first and first second wedge-forming cuts are being made.
Figure 10:
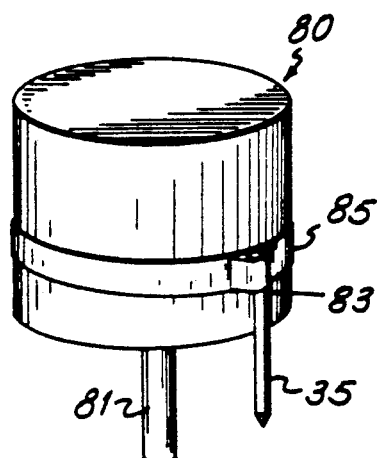
FIG. 10 is a perspective view of an electronic angular displacement reading apparatus, and means for securing it to the zero locator.

FIG. 1 shows how an arcuate osteotomy is made. The bone 10 has an angular deformity, as indicated by its crook or bend. To correct this, an arcuate cut 11 is made which extends partially across the width of bone 10 (i.e., from left to right in the figure). The arc extends from one side (the left side in FIG. 1) across about ½ to ⅓ the width of the bone. Alternatively, the arc can be centrally located in the bone, and extend from a separate cut to the left side of the bone as shown in FIGS. 10 and 12B of my previous U.S. Pat. No. 4,502,474. A wedge 12 of the bone is cut, adjacent the arc 11 and extending to the other (right) side of the bone, along two wedge-forming cuts 14 and 15. (The width of the kerf in the bone is exaggerated in the drawings for purposes of illustration.) The second wedge-forming cut 15 not yet made, is indicated by the parallel phantom lines. After wedge 12 has been removed, the two segments of bone (the portions above and below the cut in FIG. 1), are realigned by closing the gap left by removal of the wedge so that the faces of the cuts 14 and 15 are facially engaged with one another, and the bone is permitted to knit in this new orientation for correcting the angular deformation.

The amount of deformation to be removed depends, of course, on the extent of the deformation in the particular case. It can be seen by reference to FIG. 1 that the apex angle 16 of the wedge-shaped piece 12 directly controls the degree of realignment of the bone segments. In practice, the physician measures the degree of deformation of the bone, e.g. 7°, and cuts out a wedge-shaped piece having that same angularity, as nearly as possible. The apex angle 16 of the wedge-shaped piece 12 should correspond closely to the amount of deformation it is desired to remove. Thus it is important to determine the angulation of the wedge in advance, and to make the cuts 14 and 15 so that they exactly form a wedge of that angle. Once arc 11 and cut 14 have been made, the bone is severed, which would make it difficult to position the second cut 15 exactly.

Figure 2:
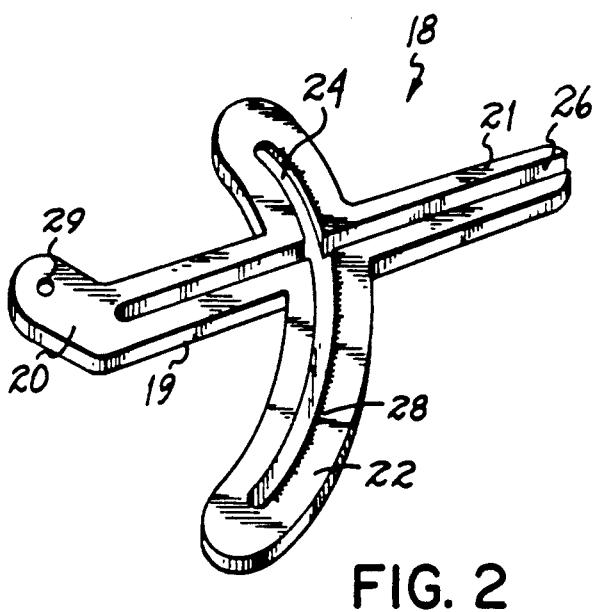
FIG. 2 is a perspective view of one form of X-guide apparatus in accordance with the invention.
Figure 3:
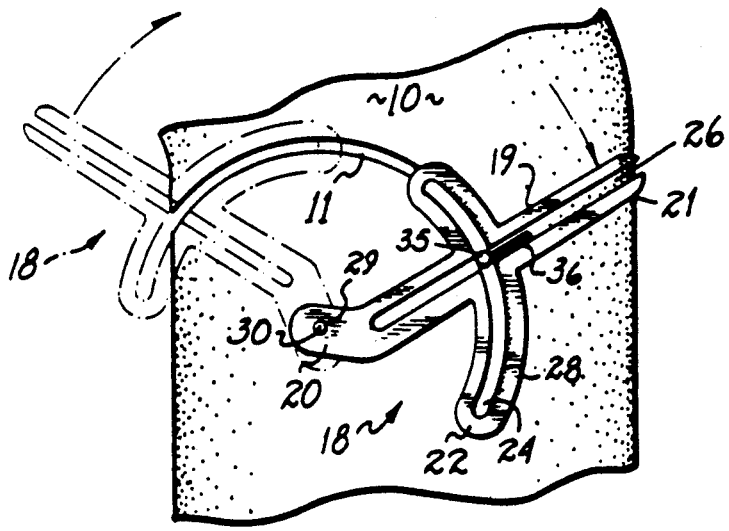
FIG. 3 is a diagrammatic plan view of the guide on a bone, and shows how the guide is positioned for making cuts.
Figure 13:
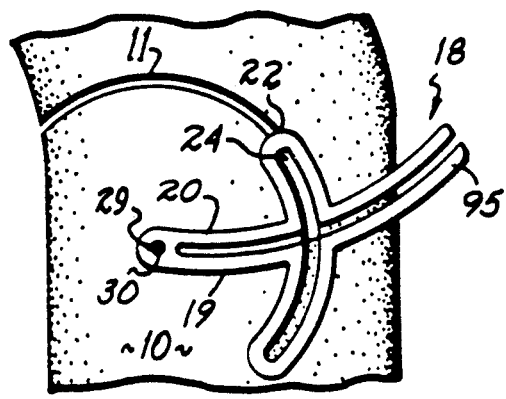
FIG. 13 is a plan view of a guide in which both slots are arcuate, the guide being positioned on a bone.
Figure 14:
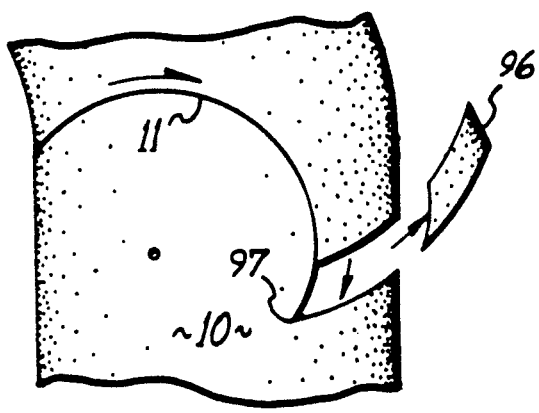
FIG. 14 is a plan view of a bone in which the wedge has been formed by arcuate cuts.

The guide 18 of this invention, shown in FIGS. 2 and 3, makes it possible to make the cuts more accurately. The guide 18, called an X-guide because of the X shape that is formed by two intersecting slots, comprises a body 19 having a pivot leg 20, an arm 21 extending from leg 20, and a cross arm 22 which extends transversely across arm 21, roughly at its midpoint. A slot 24 in cross arm 22 is a main, arcuate slot; in the embodiment shown, the slot 26 in arm 21 is a second, straight slot. As shown in FIGS. 13 and 14, the second slot can if desired be an arcuate slot, in order to form "wedges" having arcuate rather than straight sides, as in FIG. 14. As used herein, the word wedge is intended to mean the excised section of bone whether or not its sides converge.

The arcuate main slot 24 is used to guide a saw blade to form arcuate cut 11; the second slot 26 is used to guide a saw blade in making the first and second wedge-forming cuts 14 and 15. Arcuate slot 24 is formed at a specific radius of curvature about a pivot opening 29 in pivot leg 20. Thus each guide is specific for making a cut of given radius of curvature. Different sizes of guides must be used to make arcs of different radii. A scale 28, which may be calibrated in degrees, is provided on cross arm 22 to indicate the angular distance about pivot point 29, from slot 26 to points along cross slot 24.

Figure 5:
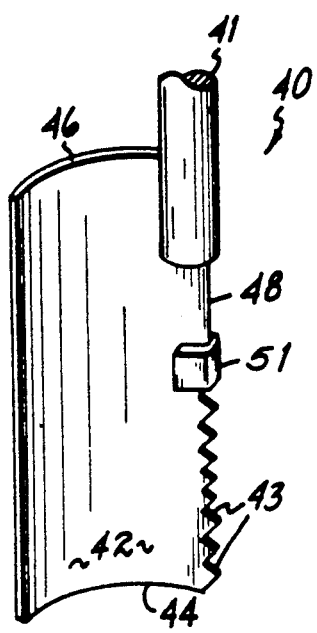
FIG. 5 is a perspective view of an arcuate saw blade in accordance with a preferred embodiment of the invention, having a shaft which is in line with the toothed leading edge of the blade.
Figure 9:
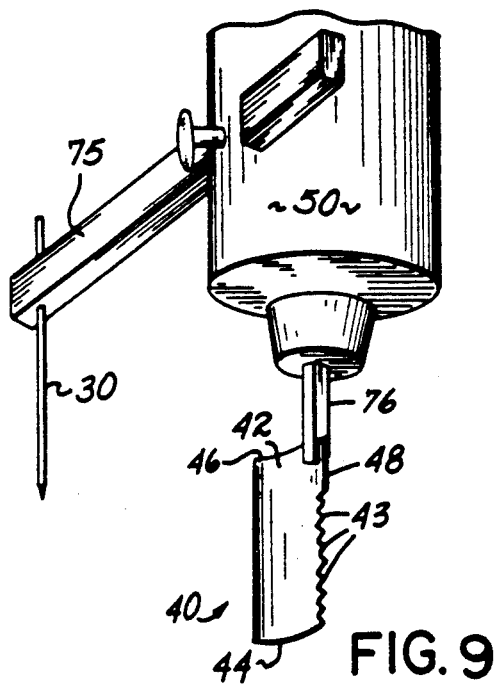
FIG. 9 is a perspective view of an arcuate bone cutting blade mounted to a reciprocating saw drive, on a swing arm.

FIG. 3 illustrates the manner in which the X-guide 18 is used to perform an arcuate osteotomy. The guide 18 is positioned on bone 10 and a bone pin 30 is inserted through pivot opening 29 so that the guide will swing about that point, and arcuate slot 24 overlies the position at which the arcuate cut is to be made. (A cap or stop, not shown, may be provided on the bone pin to prevent the guide from jumping off the pin.) The blade used to make the arcuate cut may be an oscillating saw of the type known per se, or a thin straight saw of the type known per se, or preferably a curved saw having cutting teeth along its leading edge as best shown in FIGS. 5 and 9 and described hereinafter.

The blade is passed through the arcuate slot 24, and the saw is engaged with the bone to cut it. This cut may be made completely through the bone. After the arcuate cut has been formed to the desired circumferential length, the cut is stopped and the blade removed.

The first wedge cut 14 is made using second slot 26. If this slot and cut are straight as in the FIG. 3 embodiment, a straight or planar blade will be used for the straight cut. For this purpose the saw blade is guided along straight slot 14, from the side of the bone opposite arcuate cut 11, into that cut. To make this first wedge-forming cut it is desirable that the saw not cut completely through the bone to sever it, that is, that the cut be only a partial cut and the bone remain joined rigidly by a web of bone below or at the inner end of the cut.

Figure 4:
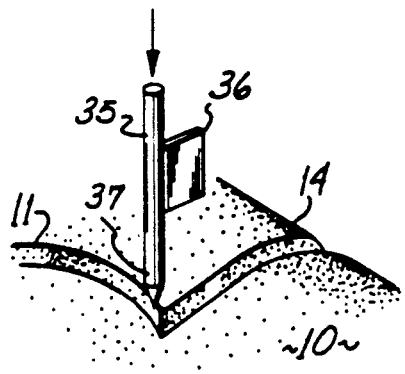
FIG. 4 is a diagrammatic perspective view of a zero locator being inserted at the juncture of the arcuate cut and the first wedge-forming cut.

Once the first wedge cut partially through the bone has been performed, the guide is then swung the desired angular distance (number of degrees) around pin 30, so that slot 26 overlies the position intended for cut 15, and that second wedge cut is made. In order to position the second cut exactly, it is preferred to use a zero locator pin of the type shown in FIG. 4. The zero locator consists of an elongated locator pin 35 which has a flag 36 projecting from it. The flag may be planar, curved or flexible to be received in the first wedge cut 14. The lower end 37 of pin 35 is inserted through the intersection of the two cuts, through slots 24 and 26, and into the end of the first wedge cut 14, as shown in FIG. 3. Flag 36 is elevated either above or below the guide so that the pin can track in slot 24 as the guide is swung past it. The flag thus indicates the position of the end of the first cut (which otherwise might not be visible). As the guide is rotated about pin 30, the angular movement of slot 26 relative to the first wedge-forming cut is indicated on scale 28. The guide is clamped, pinned, or held in this position and the second wedge-forming cut 15 is made by guiding the saw blade along slot 26.

Unlike the first wedge-forming cut, this second cut can be a through cut (if the first cut had been a through cut the bone would have been cut in two and it would be much more difficult to lay out and cut a wedge of predetermined angle). Once the second wedge cut 15 has been made, the guide can then be removed, the saw reinserted in the partially sawn first cut 14, that cut completed through the bone, and the wedge 12 removed. The two bone segments on opposite sides of the cut are then repositioned for knitting in accordance with known techniques.

Conventional arcuate osteotomy blades are toothed along the curved lower edge, and cut downwardly into the bone. While the method and guide described above do not require the use of a particular type of blade, I have also invented a blade which is especially convenient for making an arcuate cut such as that shown at 11 in FIG. 1. This blade 40, shown in FIG. 5, includes an elongated shank 41 for gripping by a linearly reciprocating saw 50 (FIG. 9), and a thin, arcuately curved blade 42. Blade 42 is cylindrically curved and has a radius of curvature which is perpendicular to its curved surface. The teeth of the blade are formed along the leading edge as designated at 43, that is, parallel to the axis of blade curvature.

This configuration is especially effective because the reciprocating movement of the blade lifts chips out of the cut, moreover, the cutting action and the arc of the cut itself is readily visible to the surgeon, yet the blade tracks accurately in the cut.

Referring to FIG. 5, it should be noted that the shank 41 is positioned directly in line with the toothed leading edge 43. The driving force of the saw motor, applied through shank 41, is thus directly in line with the teeth. This untoothed shank portion is preferred because it provides better rigidity and minimizes the tendency of the blade to bend, twist or buckle in cutting, although the shank can alternatively be circumferentially offset from leading edge 43. The shank can be set rearwardly of the blade, for example at the midpoint of the upper edge 46.

As mentioned previously, the blade is passed through the arcuate slot of the guide to make the cut 11. The engagement of the saw teeth and the saw guide would of course tend to cut or at least abrade the guide as well as the bone. For that purpose it is desirable that there be an untoothed portion 48 along the leading edge, between the shank 41 and the teeth 43, wherein the blade will pass through the guide without cutting.

The amplitude of blade reciprocation is small, e.g., about 0.10–0.13 inches. Reciprocating motor drives specifically made for osteotomies, as designated at 50 in FIG. 9, are available commercially, having a stroke with this approximate range. The toothless blade portion 48 should be slightly greater than the amplitude of the reciprocation.

In order to provide a positive indication as to where the teeth are in relation to the guide and to avoid abrasion of the guide, a stop or limit 51 is preferably secured to or provided on the blade just below the guide. This may comprise a stop in the form of a U-shaped clamp 51 which is secured onto the blade over the cutting edge, or a band of resilient material (such as an elastic), placed on the blade once the blade has been inserted through the arcuate slot 24. Alternatively, the stop may be a crimp, detent or bump formed in the blade or shank.

Figure 6:
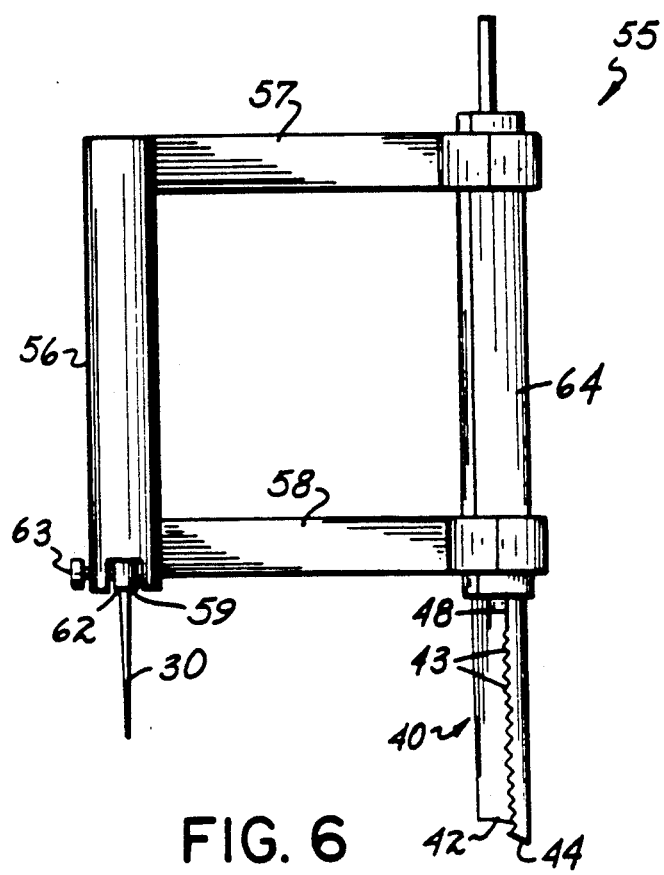
FIG. 6 is a side elevation of a double swing arm for guiding a saw blade perpendicularly along an arcuate path.
Figure 7:
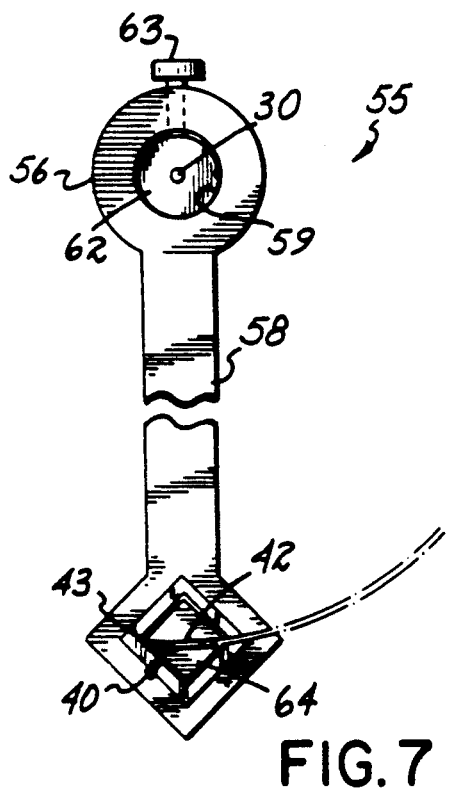
FIG. 7 is a bottom view of the swing arm shown in FIG. 6.

FIG. 6 shows another aspect of the invention, in which a reciprocating saw blade (which may be but is not necessarily, of the type designated by 40 in FIG. 5) is held at vertically spaced positions by parallel swing arms, to swing along an arcuate path. This arrangement can be used instead of an X-guide 18, for cutting an arc to a specific radius. The guide 55 comprises a main body post 56 from which vertically spaced arms 57 and 58 project parallel to one another, to provide upper and lower guides. (The guides can alternatively be provided in a continuous body rather than on spaced arms.) Post 56 has a socket 59 in which the head 62 of bone pin 30 is seated and secured as by a set screw 63, or the post 56 can have an elongated axial bore to accommodate a long bone pin 30. The saw blade used in this embodiment should have a rectangular or other non-circular shaft portion at 64 (see FIG. 7) which is received and guided in correspondingly shaped sleeve bearings in the arms 57 and 58. The non-circular shape of the blade shaft portion 64 prevents the curved blade from turning in the arms. The distance between the pin 30 and the blade 40 should correspond to the radius of curvature of blade 40. The provision of spaced bearings or guides maintains the blade in a constant vertical position so that a vertical, uniform curved cut such as arcuate cut 11 in FIG. 1 can be formed, which will provide closely mating faces for bone regrowth.

Figure 8:
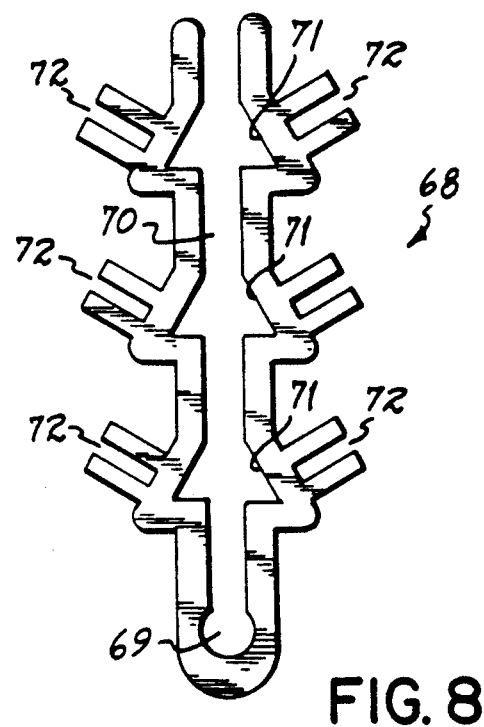
FIG. 8 is a plan view of a another form of swing arm, for making arcuate cuts of various predetermined radii and for aligning wedge-forming cuts at acute angles to the arcuate cut.

FIG. 8 shows a related type of guide for forming arcuate cuts, which has "starter" slots for forming straight wedge-forming cuts at predetermined angles in relation to the arcuate cut. The guide 68 in FIG. 8 has a pivot hole 69 for bone pin, a straight main slot 70, and non-circular cutouts 71 (in this instance, triangular in cross section) for receiving non-circular shaft of a saw blade. Wedge-forming cut locator slots 72 project angularly at each shaft guide. This guide does not guide the blade along the entire length of the wedge-forming slots, but rather merely indicates their orientation with respect to the arcuate cut around pivot 69.

Alternately, one can use a reciprocating saw motor 50 mounted on a swing arm 75 which at its opposite or fixed end is secured to a bone pin 30. As shown, the motor is fitted with an arcuate blade 40, having a triangularly sectioned shaft 76. The arc is formed as the blade swings around pin 30.

If using the X-guide 18, the angular displacement between the first and second wedge-forming cuts 14 and 15 is measured, for example by reference to scale 28 on the guide (FIG. 2). It is also contemplated that the angular displacement can be measured electronically and digitized or displayed on a screen. This can be done by use of a potentiometer 80 or similar transducer having a rotatable shaft 81 which is mounted coaxially with bone pin 30 at pivot point 30 in FIG. 1, as described in my U.S. Pat. No. 4,664,102. An end 83 of locator pin 35 is secured to the body of the potentiometer as by a strap or band 85. The radial distance between the center of potentiometer shaft 81 and the center of locator pin 35 proportionately corresponds to the radius of arcuate slot 24.

Figure 11:
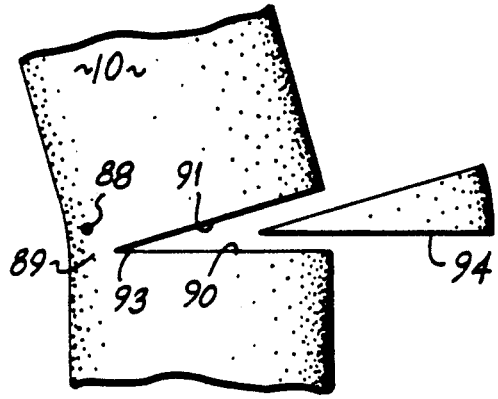
FIG. 11 is a diagrammatic view of a bone showing the removal of a simple wedge or pie-shaped segment, without an arcuate cut.
Figure 12:
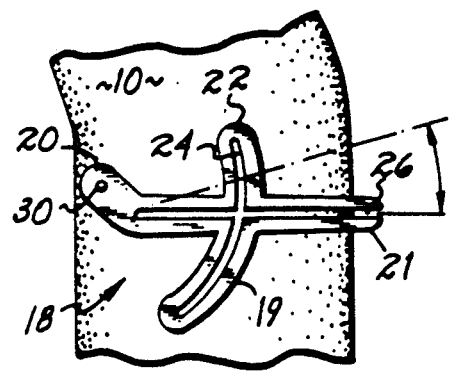
FIG. 12 is a diagrammatic view showing the use of the X-guide in the layout and cutting of a simple wedge.

FIGS. 11 and 12 show diagrammatically how a conventional wedge osteotomy (having no arcuate cut) is formed by use of the X-guide 18. The pivot 29 of the guide is fixed to the bone as at pivot point 88 by means of a bone pin, and a first cut is made to demarcate one side 90 of a wedge by guiding a saw blade along the slot 26 of the guide. This cut can be made completely through the bone, with a thin portion or web 89 of bone at the inner end of the cut to hold the bone together against separating. The guide is then pivoted the desired number of degrees around point 88, as indicated by a zero locator, and a second side 91 of the wedge is cut. The two cuts intersect at an apex 93, thereby freeing a wedge-shaped piece 94 which is removed. It should be noted that the apex 93 is offset from pivot point 88; this is desirable because the hole for bone pin 30 does not tend to undercut or further weaker the bone at the apex, an area that tends to fracture on closing the gap made by wedge removal. FIG. 12 illustrates the position of the guide for making the first cut in the wedge osteotomy of FIG. 11.

As already noted, the wedge-forming cuts can be arcuate rather than straight. FIGS. 13 and 14 show the formation of such a wedge. For this purpose the second slot 95 of the guide is arcuate, as is the first slot 24. The first cut 11 preferably is extended so that it begins to return toward the left side of the bone 10, as seen in FIG. 14, thereby forming an undercut as at 97. This tends to prevent bone separation during regrowth. At least one of the wedge-forming cuts extends to the end of the undercut on arc 11.

Having described the invention, what is claimed is:

1. A bone saw blade which is cylindrically curved about an axis of curvature,
    said blade having bone-cutting teeth along an edge thereof for cutting when said blade is reciprocated in a direction parallel to said axis of curvature,
    said blade having a shank member attached to it which is parallel to said axis of curvature.
2. The blade of claim 1 wherein said shank is in line with said teeth.
3. The blade of claim 1 wherein said edge is straight, parallel to said axis of curvature.
4. The blade of claim 1 wherein said shank has a non-circular section which prevents said shank from turning with respect to a guide through which said shank extends in use.
5. The blade of claim 1 wherein said blade has an untoothed portion along said edge, between said teeth and said shank.
6. The blade of claim 5 further including a limiting stop affixed to said blade between said untoothed portion and said teeth, said stop preventing said teeth from cutting a guide.
7. The blade of claim 6 wherein said stop is U-shaped and is secured on said edge.

* * * * *